(12) United States Patent
Ogawa et al.

(10) Patent No.: US 7,470,229 B2
(45) Date of Patent: Dec. 30, 2008

(54) ENDOSCOPE APPARATUS AND ILLUMINATING APPARATUS FOR ENDOSCOPE

(75) Inventors: Kiyotomi Ogawa, Fuchu (JP); Yutaka Konomura, Tachikawa (JP)

(73) Assignee: Olympus Corporation (JP)

( * ) Notice: Subject to any disclaimer, the term of this patent is extended or adjusted under 35 U.S.C. 154(b) by 11 days.

(21) Appl. No.: 11/616,676

(22) Filed: Dec. 27, 2006

(65) Prior Publication Data

US 2007/0147033 A1 Jun. 28, 2007

(30) Foreign Application Priority Data

Dec. 28, 2005 (JP) ............................. 2005-380211

(51) Int. Cl.
*A61B 1/07* (2006.01)
(52) U.S. Cl. .................. 600/180; 600/178; 600/182; 600/177; 362/84; 250/484.4
(58) Field of Classification Search ................ 600/178, 600/180, 182, 118, 129, 176, 177; 250/483.1, 250/484.4; 362/574, 572, 84, 260
See application file for complete search history.

(56) References Cited

U.S. PATENT DOCUMENTS

| | | | | | |
|---|---|---|---|---|---|
| 4,448,547 | A | * | 5/1984 | Wickersheim | 374/131 |
| 5,037,615 | A | * | 8/1991 | Kane | 422/82.08 |
| 5,079,678 | A | * | 1/1992 | Parker | 362/84 |
| 5,606,163 | A | * | 2/1997 | Huston et al. | 250/337 |
| 6,079,861 | A | * | 6/2000 | Woodward et al. | 362/552 |
| 6,114,704 | A | * | 9/2000 | Buck | 250/372 |
| 6,814,699 | B2 | * | 11/2004 | Ross et al. | 600/179 |
| 2004/0147809 | A1 | * | 7/2004 | Kazakevich | 600/178 |
| 2006/0069313 | A1 | * | 3/2006 | Couvillon et al. | 600/179 |
| 2006/0116553 | A1 | * | 6/2006 | Dunki-Jacobs et al. | 600/179 |
| 2006/0152926 | A1 | * | 7/2006 | Hama et al. | 362/231 |
| 2006/0235277 | A1 | * | 10/2006 | Ohkubo et al. | 600/179 |

FOREIGN PATENT DOCUMENTS

| | | |
|---|---|---|
| JP | 3194660 | 7/2001 |
| JP | 2005-205195 | 8/2005 |

* cited by examiner

*Primary Examiner*—John P Leubecker
(74) *Attorney, Agent, or Firm*—Ostrolenk, Faber, Gerb & Soffen, LLP

(57) ABSTRACT

This endoscope apparatus comprises an insertion section to be inserted into a space to be inspected, a light emitting device for illuminating inside of the space, a fluorescent member provided at a tip-end of the insertion section and emitting fluorescent light with light from the light emitting device as excitation light, a light guide transmitting the light from the light emitting device to the fluorescent member, a light branching member for branching a part of the fluorescent light returned from the fluorescent member, and an optical sensor for detecting light from the light branching member, and when the illumination light becomes dark due to a failure or removal of the tip-end section of the endoscope, an image with low luminance is not displayed, glare at replacement of the tip-end section can be reduced to improve workability and the diameter of the insertion section can be thinned.

18 Claims, 4 Drawing Sheets

ENDOSCOPE APPARATUS AND ILLUMINATING APPARATUS FOR ENDOSCOPE

This application claims benefit of Japanese Patent Application No. 2005-380211 filed in Japan on Dec. 28, 2005, the contents of which are incorporated by this reference.

BACKGROUND OF THE INVENTION

1. Field of the Invention

The present invention relates to an endoscope apparatus which can illuminate a space to be inspected and an illuminating apparatus for an endoscope.

2. Description of the Related Art

An endoscope apparatus has been widely used for observing inside of a living body and a machine. As a light source for the endoscope apparatus, a lamp with relatively large power consumption such as a halogen lamp, a xenon lamp and a metal halide lamp has been used. Recently, an endoscope apparatus has been developed using a semiconductor light-emitting device with low power consumption such as a light emitting diode (LED) and a laser diode (LD) as a light source. For example, an endoscope apparatus for fluorescent observation using an LD as a light source is proposed in Japanese Patent No. 3194660. Also, an endoscope apparatus for transmitting laser light from the LD to a fluorescent member provided at a tip-end section by an optical fiber and illuminating inside the space to be inspected with white light converted by the fluorescent member from the light is proposed in Japanese Unexamined Patent Application Publication No. 2005-205195.

SUMMARY OF THE INVENTION

One of endoscope apparatuses according to the present invention comprises an insertion section to be inserted into a space to be inspected, a light emitting device to be a light source for illuminating inside of the space to be inspected, a fluorescent member provided at a tip-end of the insertion section and emitting fluorescent light with light from the light emitting device as excitation light, a light guide provided in the insertion section and transmitting the light from the light emitting device to the fluorescent member, a light branching member for branching a part of the fluorescent light returned from the fluorescent member through the light guide, and an optical sensor for detecting light from the light branching member.

Another one of the endoscope apparatuses according to the present invention comprises an insertion section to be inserted into a space to be inspected, a light emitting device to be a light source for illuminating inside of the space to be inspected, a tip-end optical adapter which can be detachably attached to the tip-end of the insertion section, a fluorescent member provided at the tip-end optical adapter and emitting fluorescent light with light from the light emitting device as excitation light, a light guide provided in the insertion section and transmitting the light from the light emitting device to the fluorescent member, a light branching member for branching a part of the fluorescent light returned from the fluorescent member through the light guide, and an optical sensor for detecting light from the light branching member.

An illuminating apparatus for an endoscope according to the present invention comprises a light emitting device to be a light source for illuminating inside of the space to be inspected, a fluorescent member for emitting fluorescent light with light from the light emitting device as excitation light, a light guide for transmitting the light from the light emitting device to the fluorescent member, a light branching member for branching a part of the fluorescent light returned from the fluorescent member through the light guide, and an optical sensor for detecting light from the light branching member.

Other features and advantages of the present invention will be made apparent from the description below.

DESCRIPTION OF THE PREFERRED EMBODIMENTS

Embodiments of the present invention will be described using the attached drawings.

First, a first embodiment of the present invention will be described using FIGS. 1 to 3.

Figure 1:
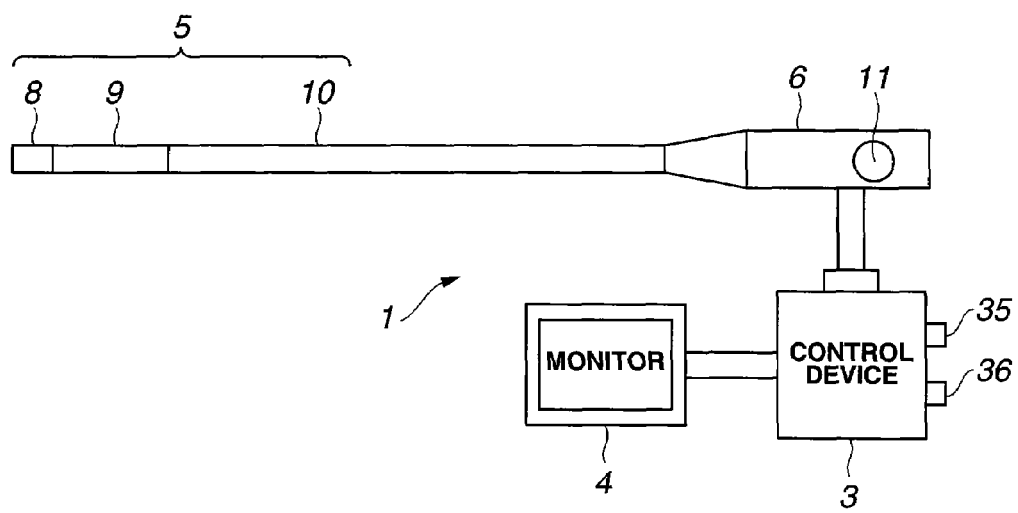
FIG. 1 is an appearance diagram showing an outline of an endoscope apparatus of a first embodiment of the present invention.

As shown in FIG. 1, an endoscope apparatus 1 of this embodiment comprises in outline a control device 3 incorporating a control portion for controlling the entire device and a light source portion for illuminating the inside of the space to be inspected, a monitor 4 connected to the control device 3 for observation, an elongated insertion section 5 to be inserted into the space to be inspected, an operation portion 6 located at the base end side (hand side of an operator) of the insertion section 5 and gripped by the operator for operating the insertion section 5, and a flexible universal cord 7 extended from the operation portion 6 and connected to the control device 3.

The endoscope apparatus 1 is an industrial endoscope apparatus with which an image of the space can be observed by the monitor 4 by inserting the insertion section 5 into the space to be inspected such as an inside of a machine or image data of the image can be taken in. And the device with the same configuration as above can be applied to an endoscope apparatus for observing not inside the machine but inside a living body. In this case, the space to be inspected is the inside of a living body.

The insertion section 5 comprises a tip-end section 8 incorporating an image pickup device for forming an observation image of a subject for capturing an image and a light source portion, etc., a bending section 9 formed capable of being bent with a plurality of bending pieces consecutively connected capable of pivotal rotation, and a flexible section 10 formed by an elongated flexible members. The bending section 9 is bent by operating a bending knob 11 disposed on the operation portion 6. In the control device 3, a main switch 35, which is a power switch of the entire endoscope apparatus 1, and a lamp switch 36, which is a switch of the light source portion, are arranged.

Figure 2:
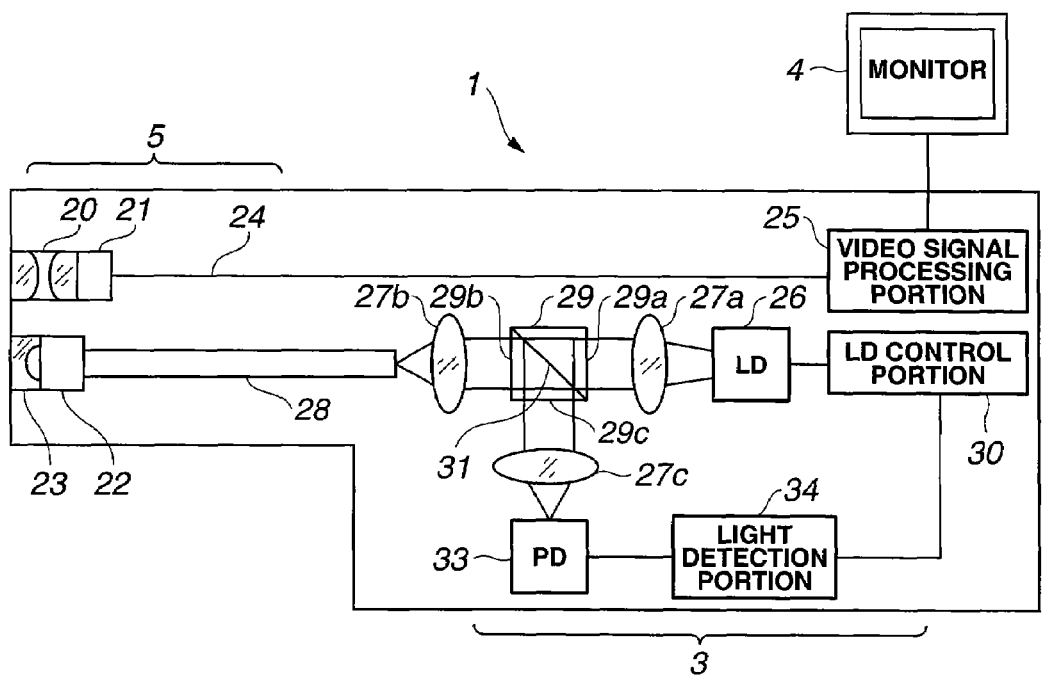
FIG. 2 is a block diagram of the endoscope apparatus in FIG. 1.

Describing the internal configuration of the endoscope apparatus 1 by FIG. 2, inside the tip-end section 8, there are provided an objective optical system 20 for forming an observation image of a subject, a CCD 21 of an image pickup device made of a charge coupled device in which the observation image is formed and the observation image is converted to an electric signal, a fluorescent member 22 for emitting illumination light for illuminating the inside of the space to be inspected as a light source portion, and an illumination optical system 23 for controlling light of the illumination light.

The tip-end section 8 and the operation portion 6 are connected to each other by the bending section 9, the flexible section 10 and moreover, the operation portion 6 and the control device 3 are connected to each other by the universal cord 7. And into the bending section 9, the flexible sections 10 and the universal cord 7, a video signal line 24 connected to the CCD 21 and an optical fiber 28 as a light guide are inserted. The optical fiber 28 is connected to the fluorescent member 22 with the tip-end side disposed at the tip-end section 8, and the base end side is faced with a focus position of a light collecting optical system 27b.

The control device 3 comprises a video signal processing portion 25 to which a video signal line 24 is connected and a light source portion, and the light source portion has an LD control portion 30 (hereinafter described as LD), which is a light source control portion for drive-controlling an laser diode as a light emitting device 26, the LD 26, a light collecting optical system 27a disposed in front of the LD 26, a light collecting optical system 27b, a light splitter 29, which is a light branching member disposed between the light collecting optical systems 27a and 27b, a light collecting optical system 27c disposed on the side of the light splitter 29, a photo diode (hereinafter described as PD) 33 as an optical sensor disposed at the focus position of the light collecting optical system 27c, and a light detection portion 34 which takes in an output signal of the PD 33 and outputs the light detection signal to the LD control portion 30.

The LD 26 is a laser diode which can emit blue laser light with the oscillation wavelength of 445 nm, for example, and disposed at the focus position of the light collecting optical system 27a.

The light splitter 29 is comprised by two right angle prisms, and on an inclined face of one of the prisms a reflective film 31 with wavelength selectivity is vapour-deposited. And the inclined faces of the two prisms are bonded into a cube shape.

The reflective film 31 is a thin film which transmits blue laser light outputted by the LD 26 and reflects light with a wavelength longer than that. An end face of the light splitter 29 on the light collecting optical system 27b side to which the light enters from the fluorescent member 22 is made as an input end 29b. An end face on the light collecting optical system 27a side to which the light of the LD 26 enters is made as an output end 29a. An end face on the light collecting optical system 27c side on the PD 33 side is made as an output end 29c.

The fluorescent member 22 is a fluorescent member emitting fluorescent light of red light and green light with the blue laser light by the LD 26, which is the light emitting device, as excitation light. The fluorescent light by the red light and green light is mixed with the blue laser light diffused in the fluorescent member 22 to become white light and illuminates inside the space to be inspected through the illumination optical system 23.

The optical fiber 28 has its base end section located at the focus of the light collecting optical system 27b and the tip-end section is connected to the fluorescent member 22.

In the endoscope apparatus 1 having the above-mentioned configuration, an image of the inspection subject illuminated by the light source portion in the state where the main switch 35 is on and the lamp switch 36 is on is converted to a video signal at the CCD 21 and inputted to the video signal processing portion 25 through the video signal line 24. The video signal obtained at the video signal processing portion 25 is converted to a TV signal and outputted to the monitor 4 and displayed thereon.

At the light source portion of the endoscope apparatus 1, the LD 26 is lighted under control of the LD control portion 30 by turning on the lamp switch 36. A blue laser light with the wavelength of 445 nm is diffused and emitted from the LD 26, and enters as parallel light from the light collecting optical system 27a for collecting light into substantially parallel light to the output end 29a of the light splitter 29. Since the blue laser light having entered from the output end 29a is transmitted through the reflective film 31, most of the light is emitted from the input end 29b.

The blue laser light emitted from the input end 29b of the light splitter 29 is focused on the base end section of the optical fiber 28 by the light collecting optical system 27b and irradiates the fluorescent member 22 through the optical fiber 28.

At the fluorescent member 22, fluorescent light of red light and green light is emitted with the blue laser light as excitation light by action of a fluorescent body included in the fluorescent member 22. The red light and the green light are mixed with the blue laser light transmitted through the fluorescent member 22 and white light is emitted from the fluorescent member 22 so that it passes through the illumination optical system 23 and illuminates the space to be inspected. The illumination light is reflected by the inspection subject and its subject image passes through the objective optical system 20 and is taken in and forms an image on an image forming face of the CCD 21.

On the other hand, a part of the white light from the fluorescent member 22 reaches the base end side through the optical fiber 28 and enters the light splitter 29 from the input end via the light collecting optical system 27b. In that incident light, the light with the wavelength longer than that of the blue laser light outputted by the LD 26 is reflected by the reflective film 31 and emitted from the output end 29c as detection light. The detection light enters the PD 33 through the light collecting optical system 27c, and a detection signal is outputted from the PD 33. The detection signal is taken into the LD control portion 30 through the light detection portion 34.

The LD control portion 30 determines if the detection signal is equal to or above a predetermined level (level corresponding to a luminance state enabling observation). The LD control portion 30 recognizes that the LD 26, the optical fiber 28 and the fluorescent member 22 are in the normal operating state and the space to be inspected is in the illuminated state capable of being observed based on the determination. And continuation of observation or photographing by the endoscope apparatus 1 is permitted.

However, if there is some nonconformity in the tip-end section 8 of the insertion section 5, the optical fiber 28 or the LD 26, or if white light to the base end side disappears due to removal of the tip-end section 8 or drops below a predetermined level, the drop of the detection output is detected by the PD 33, and the LD control portion 30 immediately stops light emission of the LD 26 or switches to a low output state to an extent that the laser light is not emitted, and then notify the operator that the endoscope apparatus is not capable of or suitable for observation. At that time, it is possible to instruct stop of output of the image signal with low luminance to the video signal processing portion 25.

The above-mentioned LD control processing operation by the LD control portion 30 in the endoscope apparatus 1 will be described using a flowchart of the LD control processing in FIG. 3.

Figure 3:
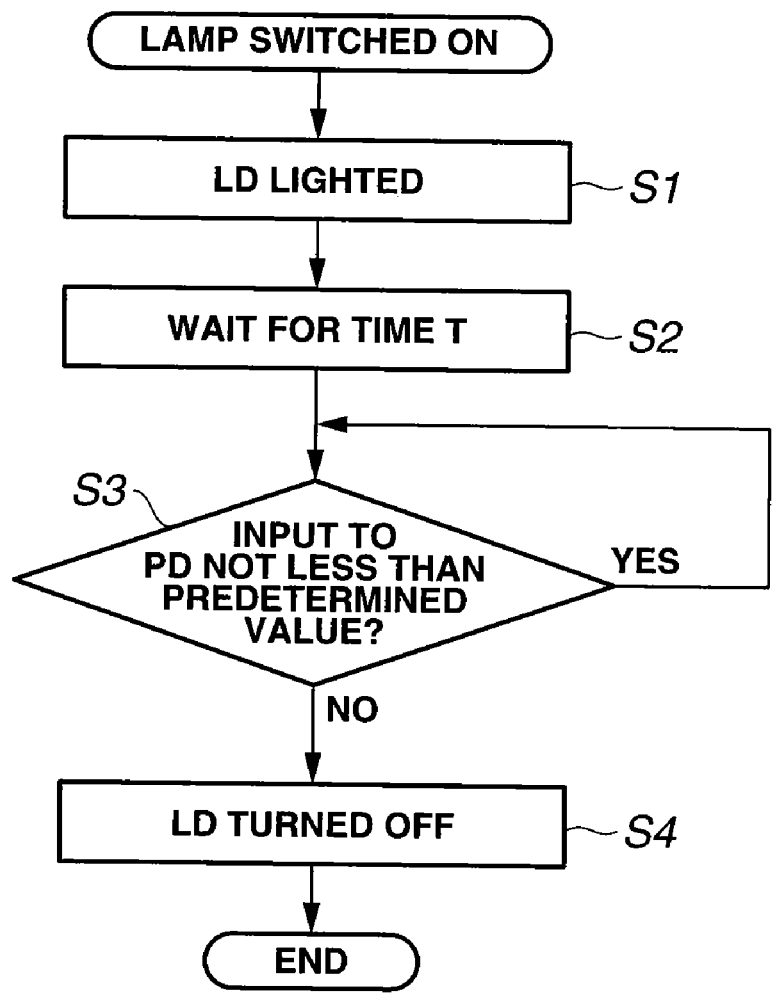
FIG. 3 is a flowchart of light source control after lamp switch-on in the endoscope apparatus in FIG. 1.

After the main switch 32 is turned on, when on-operation of the lamp switch 36 is detected by the LD control portion 30, the LD control processing shown FIG. 3 is started, and the LD 26 is lighted at step S1 so as to start illumination of the space to be inspected. At step S2, stabilization of output of the PD 33 is awaited for a predetermined time T, 10 msec, for example, and then, the input state of the light to the PD 33 is checked by the output signal at step S3. It is checked if the value of the output signal of the PD 33 is equal to or more than the predetermined value or not, or if a light amount corresponding to the state where the space to be inspected is illuminated suitably for observation is reflected from the fluorescent member 22, for example.

If it is confirmed that the output of the PD 33 is equal to or more than the predetermined value, light emission of the LD 26 is continued, and the check at step S3 is repeated. If the output of the PD 33 is decreased and it is confirmed that nonconformity occurs at the tip-end section 8 of the insertion section 5, the optical fiber 28 or the LD 26, or that the incident light amount to the PD 33 is decreased by removal of the tip-end section 8 or the like and the value falls below the predetermined value, for example, the program goes on to step S4, where the LD 26 is turned off and this routine is ended.

In the processing at step S4, the LD 26 may be controlled so that the LD 26 is not turned off but the luminance is lowered to continue lighting in the dimmed state not emitting the laser. By controlling in this way, a failure of the LD 26 itself and a failure of the other sections can be distinguished.

As mentioned above, according to the endoscope apparatus 1 of this embodiment, if the fluorescent member 22 is removed due to breakage of the tip-end section 8 of the insertion section 5 or the optical fiber 28 is broken by action of a large external force on the insertion section 5, for example, such a state is detected by the PD 33 from the decrease of light amount from the fluorescent member 22. And the light emission of the LD 26 can be stopped or brought into the dimmed state by the LD control portion 30 so that the failure at the tip-end section of the endoscope is notified to the user. At the same time, display of an image with lowered luminance by dark illumination can be avoided.

Also, at replacement work of the fluorescent member 22 or the optical fiber 28, when the tip-end section 8 is removed, by stopping or decreasing the light amount of light emission of the LD 26 as above, glare can be prevented when the user looks at the tip-end of the insertion section, which facilitates the replacement work.

Moreover, since only one optical fiber 28 can function both as a light guide for illumination and light guide for fluorescent light detection, there is no need to provide an optical sensor or a light guide exclusively for fluorescent light detection in the insertion section 5 any more, by which the diameter of the insertion section 5 can be thinned.

This embodiment is put into practice as an electronic endoscope having a flexible insertion section 5 for electrically transmitting an image. However, not limited to this, the above-mentioned light source portion can be also applied to a fiber scope having a flexible insertion section and transmitting an image by an image guide fiber. Also, the above-mentioned light source portion can be also applied to a rigid endoscope having a rigid insertion section and transmitting an image by a relay lens system, which can exert the same effect. In this embodiment, the optical fiber 28 is used as a light guide for transmitting the laser light. However, by having a blue LED as the light emitting device and applying an optical fiber bundle bundling a plurality of optical fibers instead of the optical fiber 28, the same effects can be obtained.

Moreover, in this embodiment, the light source portion is incorporated in the control device 3. However, not limited to this, it is also possible to configure such that an optical connector is disposed at the base end side of the optical fiber 28 and detachably connected as an illuminating apparatus for an endoscope having the light emitting device, light collecting optical system, the light branching member, the optical sensor, and the LD control portion through the optical connector in the state separate from the control device 3.

Next, an endoscope apparatus of a second embodiment of the present invention will be described using a block diagram of the endoscope apparatus of this embodiment in FIG. 4.

Figure 4:
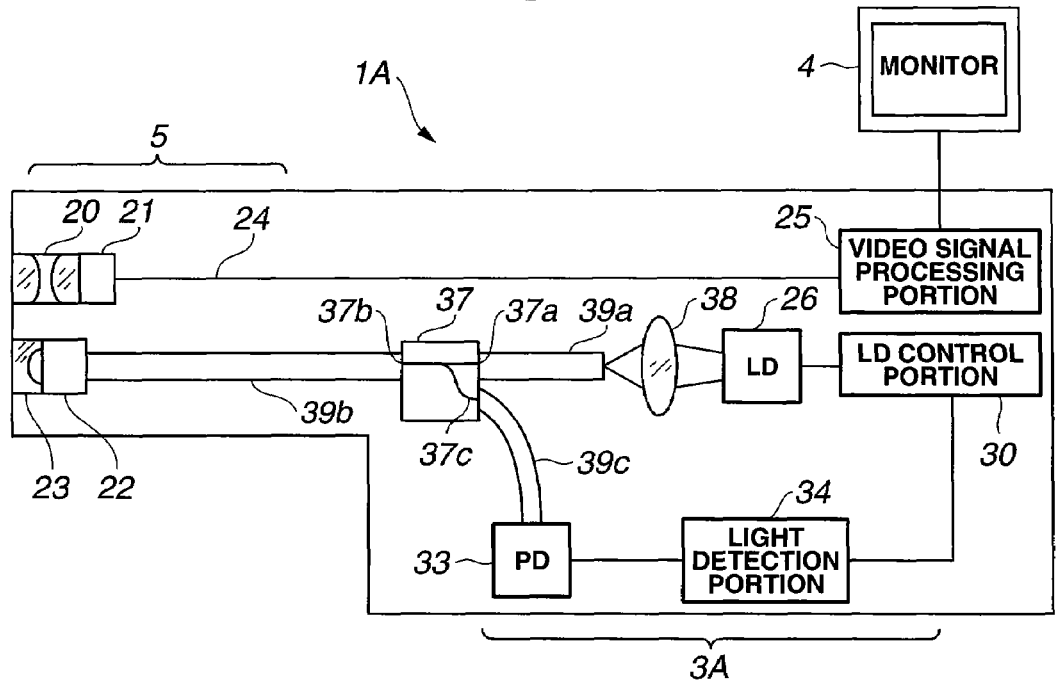
FIG. 4 is a block diagram of the endoscope apparatus of a second embodiment of the present invention.

In an endoscope apparatus 1A of this embodiment, as shown in FIG. 4, an optical fiber coupler 37 with 1-input (input end 37b), 2-output (output ends 37a, 37c) is applied as the light branching member in the light source portion to the endoscope apparatus 1 of the first embodiment in place of the light splitter 29. The same components as those in the endoscope apparatus 1 of the first embodiment are given the same reference numerals and differences will be described below.

In a control device 3A of the endoscope apparatus 1A of this embodiment, one end of an optical fiber 39a is arranged in the vicinity of a focus of the light collecting optical system 38 for collecting blue laser light with the wavelength of 445 nm, for example, diffused and emitted from the LD 26 as shown in FIG. 2. The other end of the optical fiber 39a is connected to the output end 37a of the optical fiber coupler 37. To the input end 37b of the optical fiber coupler 37, the base end side of an optical fiber 39b is connected. The tip-end side of the optical fiber 39b is connected to the fluorescent member 22 arranged at the tip-end section of the insertion section 5. To the output end 37c of the optical fiber coupler 37, one end of the optical fiber 39c is connected, while to the other end of the optical fiber 39c, the PD 33, which is an optical sensor, is connected.

In the case of illumination of the inside of the space to be inspected, the laser light emitted from the LD 26 is irradiated to the fluorescent member 22 via the light collecting optical system 38, the optical fiber 39a, the optical fiber coupler 37 and the optical fiber 39b, and the inside of the space to be inspected is illuminated by white light. On the other hand, a part of the white light from the fluorescent member 22 enters the PD 33 from the output end 37c of the optical fiber coupler 37 via the optical fiber 39c, and a detection signal is obtained. The detection signal of the PD 33 is inputted to the LD control portion 30 through the light detection portion 34.

Control operation or the like by the LD control portion 30 when the fluorescent member 22 is removed by breakage of the tip-end section 8 of the insertion section 5 or the optical fiber 39b is broken by action of a large external force on the insertion section 5 or at part replacement of the insertion section 5 is the same as that in the first embodiment.

The effect by the endoscope apparatus 1A of this embodiment is the same as that of the first embodiment, and particularly since the light branching member is made more compact than the first embodiment and the light collecting optical system for input/output with respect to the light branching member is simplified, it has an effect that the device is made compact.

In the endoscope apparatus 1A of this embodiment, the optical fiber coupler 37 is used as the light branching member, but if a light branching waveguide is used in place of that, the same effect can be obtained.

In this embodiment, too, the light source portion is incorporated in the control device 3A, but not limited to this, it may be so configured that the illuminating apparatus for an endoscope incorporating the light emitting device, the optical fiber coupler, the optical sensor, and the LD control portion is detachably attached to the endoscope apparatus in the state separate from the control device 3A.

Next, an endoscope apparatus of a third embodiment of the present invention will be described using FIGS. 5 to 7.

Figure 5:
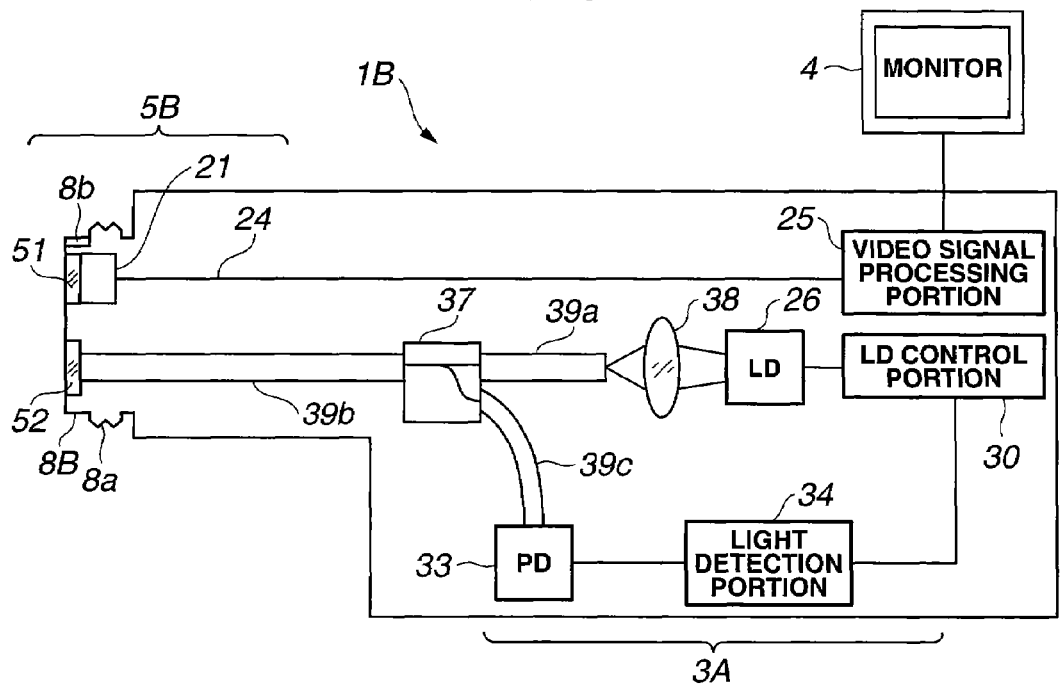
FIG. 5 is a block diagram of the endoscope apparatus of a third embodiment of the present invention showing a state where a tip-end optical adapter is removed.
Figure 6:
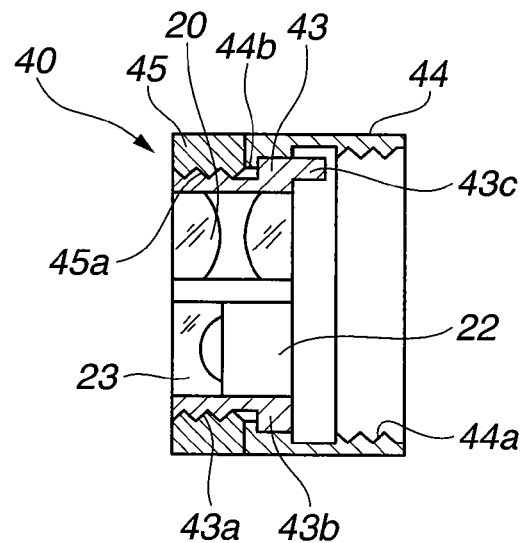
FIG. 6 is a sectional view of the tip-end optical adapter which can be detachably attached to the tip-end of an insertion section of the endoscope apparatus in FIG. 5.
Figure 7:
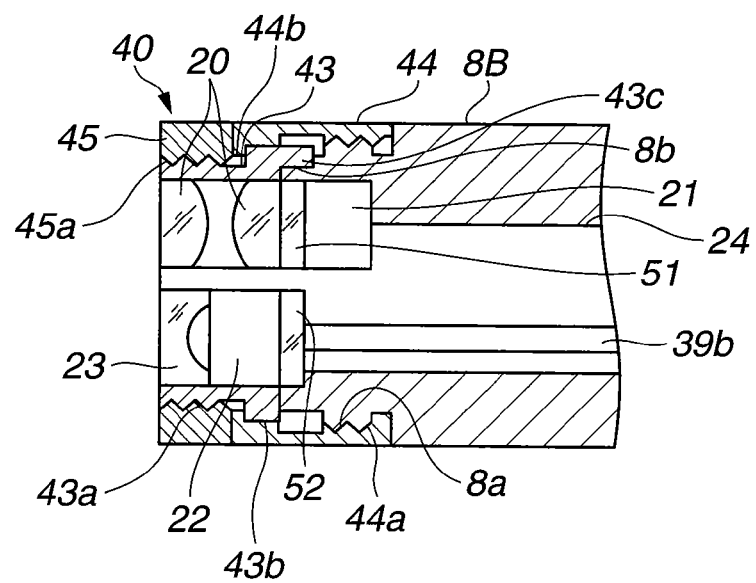
FIG. 7 is a sectional view of the tip-end optical adapter attached to the tip-end of an insertion section of the endoscope apparatus in FIG. 5.

In an endoscope apparatus 1B of this embodiment, the optical fiber coupler 37 as the light branching member is also applied to the endoscope apparatus 1A of the second embodiment as shown in FIGS. 5, 7, but they are different from each other in the point that a tip-end optical adapter 40 is made attachable to a tip-end section 8B of an insertion section 5B in the detachable state. The same components of the endoscope apparatus 1A of the second embodiment as those of the endoscope 1 in the first embodiment are given the same reference numerals and only differences will be described below.

At the tip-end section 8B of the insertion section 5B of the endoscope apparatus 1B, the CCD 21 as the image pickup device, a protective cover glass 51 for CCD protection and an optical-fiber protective cover glass 52 disposed at the tip-end section of the optical fiber 39b are arranged. Moreover, on the outer circumference of the tip-end section 8B, a male thread section 8a for attaching the tip-end optical adapter 40 and a positioning groove 8b for the tip-end optical adapter are provided.

On the other hand, the tip-end optical adapter 40 comprises a substantially columnar adapter body 43, a retaining ring 44 in the substantially cylindrical shape and a ring-shaped retainer 45.

In the adapter body 43, the objective optical system 20 for forming a subject image on the CCD 21, the fluorescent member 22 for emitting fluorescent light with the laser light from the LD 26 as excitation light, and the illumination optical system 23 in front of the fluorescent member 22 for illuminating white light emitted from the fluorescent member 22 into the space to be inspected are arranged. Moreover, on the outer circumference section, a male thread section 43a, an outer circumferential engagement section 43b in the rear of the male thread, and a positioning projection 43c projecting toward the CCD side are provided.

The retaining ring 44 has an inner circumferential engagement section 44b and a female thread section 44a on the inner circumference in the rear and is rotatably attached to the adapter body 43 by fitting the inner circumferential engagement section 44b into the outer circumferential engagement section 43b.

The retainer 45 is fixed to the front part of the adapter body 43 to which the retaining ring 44 is mounted by screwing and bonding a female thread section 45a to the male thread section 43a. In this state, the retaining ring 44 is prevented from being removed from the adapter body 43.

The above-mentioned tip-end optical adapter 40 is attached to the tip-end section 8B of the insertion section 5B of the endoscope apparatus 1B by screwing. In detail, as shown in FIG. 7, the positioning projection 43c of the adapter body 43 is fitted into the positioning groove 8b of the tip-end section 8B of the insertion section 5B. When the retaining ring 44 is screwed with the male thread section 8a and the female thread option 44a, and moreover, the outer circumferential engagement section 43b and the inner circumferential engagement section 44b are brought into contact in the axial direction and the retaining ring 44 is fixed to the tip-end section 8B, the tip-end optical adapter 40 is attached to the tip-end section 8B. In this attachment state, the objective optical system 20 is located opposite in front of the CCD 21, and the fluorescent member 22, the illumination optical system 23 are located opposite in front of the optical fiber 39b.

The tip-end optical adapter 40 can be removed from the tip-end section 8B of the insertion section 5B by loosening the thread sections 8a, 44b.

In the state where the tip-end optical adapter 40 is attached to the tip-end section 8B, the laser light emitted from the LD 26 passes through the light collecting optical system 38, the optical fiber 39a, the optical fiber coupler 37 and the optical fiber 39b, and is irradiated to the fluorescent member 22. At the fluorescent member 22, white light including the laser light with the laser light as excitation light is irradiated toward the space to be inspected.

On the other hand, a part of the white light emitted from the fluorescent member 22 goes through the optical fiber 39b, the optical fiber coupler 37 and the optical fiber 39c, and is guided to the PD 33, its detection output is inputted to the LD control portion 30 through the light detection portion 34 connected to the PD 33, and the lighting control of the LD 26 is executed.

If the tip-end optical adapter 40 is removed while the LD 26 is lighted, since the excitation light is not irradiated to the fluorescent member 22 any more, the white light stops emitting and the light guided by the PD 33 is decreased. And when the fact is recognized by the LD control portion 30 that the light amount detected at the light detection portion 34 falls below the predetermined value, the LD control portion 30 stops driving of the LD 26 or brings it into the dimmed state or the light emitting state to the extent that laser light is not emitted.

According to the endoscope apparatus 1B of this embodiment, the same effect as that of the second embodiment is exerted, and particularly since the tip-end optical adapter 40 is replaceable, replacement of the fluorescent member 22, the objective optical system 20 and the illumination optical system 23 is easy. And by replacing the fluorescent member 22 by another florescent member, the illumination light with the wavelength suitable for the space to be inspected can be switched to the state capable of irradiation. Also, by replacing the objective optical system 20, the characteristic of the objective optical system 20 can be changed so that an optimal view angle, observation direction and focal depth according to the inspection subject can be selected.

Moreover, when the tip-end optical adapter 40 is removed, since lighting of the LD 26 is stopped or brought into the dimmed state, an operator can replace the tip-end optical adapter without sensing a glare. Also, in the above dimmed state, it can be determined if the LD 26 is defective or not.

For attachment of the tip-end optical adapter 40 to the tip-end section 8B, locking structure by screws or engagement of notches and projections can be employed other than the above-mentioned screwing of threads.

The LD 26 applied as the light emitting device in each of the above-mentioned embodiments is a laser diode which can emit blue laser light with the oscillation wavelength of 445 nm, but it may be an LD emitting blue laser light with the oscillation wavelength in a range of 235 to 500 nm or ultraviolet laser light. Moreover, a light emitting diode (LED) may be applied in place of the LD, and a light emitting diode emitting blue light with the oscillation wavelength of the main light-emitting peak in a range of 235 to 500 nm or ultraviolet ray can exert the same effect.

If the light emitting device is an LD emitting the ultraviolet laser light or an LED emitting the ultraviolet ray as above, the fluorescent member 22 emits white fluorescent light with the light emitted by the light emitting device as excitation light. Also, if the light emitting device is a blue-light LED, the fluorescent member 22 emits red light and green light with the blue light as excitation light, and white fluorescent light mixed with the blue light is emitted.

According to the endoscope apparatus or the illuminating apparatus for an endoscope of the present invention, when the illumination light becomes dark due to a failure, removal or the like of the endoscope tip-end section, an image with low luminance is not displayed, glare at replacement of the tip-end section is reduced so as to improve workability and the diameter of the insertion section can be thinned.

The present invention is not limited to each of the above embodiments, but various variations are possible in a range not departing from its gist in practice. Moreover, inventions in various stages are included in each embodiment, and various inventions can be extracted in appropriate combinations of the disclosed plurality of constituent features.

For example, even if some constituent features are deleted from all the constituent features shown in each embodiment, if the problems described in the problems to be solved by the invention can be solved and the effects described in the effect of the invention can be obtained, the configuration from which the constituent features are deleted can be extracted as the invention.

What is claimed is:

1. An endoscope apparatus comprising:
    an insertion section to be inserted into a subject to be inspected;
    an image pickup device for taking an observation image of the subject;
    a video signal processing portion for processing the observation image;
    a display device for displaying at least the observation image;
    a light emitting device being a light source for illuminating the subject;
    a fluorescent member provided at a tip-end of the insertion section and emitting fluorescent light with light from the light emitting device as excitation light;
    a light guide provided in the insertion section and transmitting the light from the light emitting device to the fluorescent member;
    a light branching member for branching a part of the fluorescent light returned from the fluorescent member through the light guide;
    an optical sensor for detecting light from the light branching member; and
    a control portion for controlling the light emitting device according to a detection result of the optical sensor,
    wherein the control portion is for controlling the video signal processing portion according to the detection result of the optical sensor.

2. The endoscope apparatus according to claim 1,
    wherein the light emitting device is a laser diode which emits laser light with an oscillation wavelength in a range of 235 to 500 nm.

3. The endoscope apparatus according to claim 1, wherein the light emitting device is a light emitting diode emitting light with an oscillation wavelength of the main light emitting peak in a range of 235 to 500 nm.

4. The endoscope apparatus according to claim 1,
    wherein at the fluorescent member, fluorescent light emitted with light from the light emitting device as excitation light is white light.

5. The endoscope apparatus according to claim 1,
    wherein the fluorescent member includes a fluorescent body in which a combination of the fluorescent light and the excitation light is white light.

6. The endoscope apparatus according to claim 1, wherein the control portion controls the light emitting device not to emit the excitation light or to be in a dimmed state when an output of the optical sensor is decreased.

7. The endoscope apparatus according to claim 6,
    wherein the control portion controls the video signal processing portion not to output the observation image to the display device.

8. The endoscope apparatus according to claim 6,
    wherein the control portion controls the video signal processing portion to output a notification to the display device.

9. The endoscope apparatus according to claim 1, further comprising:
    an object optical system for forming the observation image on the image pickup device; and
    an illumination optical system for light distribution,
    wherein the object optical system and the illumination optical system are located at the tip-end of the insertion section.

10. An endoscope apparatus comprising:
    an insertion section to be inserted into a subject to be inspected;
    an image pickup device for taking an observation image of the subject;
    a video signal processing portion for processing the observation image;
    a display device for displaying at least the observation image;
    a light emitting device being a light source for illuminating the subject;
    a tip-end optical adapter which can be detachably attached to a tip-end of the insertion section;
    a fluorescent member provided at the tip-end optical adapter and emitting fluorescent light with light from the light emitting device as excitation light;
    a light guide provided in the insertion section and transmitting light from the light emitting device to the fluorescent member;
    a light branching member for branching a part of the fluorescent light returned from the fluorescent member through the light guide;
    an optical sensor for detecting light from the light branching member; and
    a control portion for controlling the light emitting device according to a detection result of the optical sensor,
    wherein the control portion is for controlling the video signal processing portion according portion according to the detection result of the optical sensor.

11. The endoscope apparatus according to claim 10,
    wherein the light emitting device is a laser diode which emits laser light with an oscillation wavelength in a range of 235 to 500 nm.

12. The endoscope apparatus according to claim 10,
wherein the light emitting device is a light emitting diode emitting light with an oscillation wavelength of the main light emitting peak in a range of 235 to 500 nm.

13. The endoscope apparatus according to claim 10,
wherein at the fluorescent member, fluorescent light emitted with light from the light emitting device as excitation light is white light.

14. The endoscope apparatus according to claim 10,
wherein the fluorescent member includes a fluorescent body in which a combination of the fluorescent light and the excitation light is white light.

15. The endoscope apparatus according to claim 10,
wherein the control portion controls the light emitting device not to emit the excitation light or to be in a dimmed state when an output of the optical sensor is decreased.

16. The endoscope apparatus according to claim 15,
wherein the control portion controls the video signal processing portion not to output the observation image to the display device.

17. The endoscope apparatus according to claim 15,
wherein the control portion controls the video signal processing portion to output a notification to the display device.

18. The endoscope apparatus according to claim 10, further comprising:
an object optical system for forming the observation image on the image pickup device; and
an illumination optical system for light distribution,
wherein the object optical system and the illumination optical system are located at the tip-end of the insertion section.

* * * * *